(12) United States Patent
Chen et al.

(10) Patent No.: US 11,078,184 B2
(45) Date of Patent: Aug. 3, 2021

(54) DEXRABEPRAZOLE SODIUM COMPOUND AND PHARMACEUTICAL COMPOSITION THEREOF

(71) Applicants: JIANGSU AOSAIKANG PHARMACEUTICAL CO., LTD., Jiangsu (CN); NANJING HAIRUN PHARMACEUTICAL CO., LTD., Jiangsu (CN)

(72) Inventors: Xiangfeng Chen, Nanjing (CN); Hongyu Chen, Nanjing (CN); Xiaoxin Li, Nanjing (CN); Xun Pan, Nanjing (CN); Min Sun, Nanjing (CN)

(73) Assignees: JIANGSU AOSAIKANG PHARMACEUTICAL CO., LTD., Nanjing (CN); NANJING HAIRUN PHARMACEUTICAL CO., LTD., Nanjing (CN)

( * ) Notice: Subject to any disclaimer, the term of this patent is extended or adjusted under 35 U.S.C. 154(b) by 13 days.

(21) Appl. No.: 16/624,740

(22) PCT Filed: Jun. 22, 2018

(86) PCT No.: PCT/CN2018/092347
§ 371 (c)(1),
(2) Date: Dec. 19, 2019

(87) PCT Pub. No.: WO2018/233678
PCT Pub. Date: Dec. 27, 2018

(65) Prior Publication Data
US 2020/0216414 A1    Jul. 9, 2020

(30) Foreign Application Priority Data

Jun. 23, 2017 (CN) .......................... 201710485939.5
Jun. 23, 2017 (CN) .......................... 201710487802.3

(51) Int. Cl.
*C07D 401/12* (2006.01)
(52) U.S. Cl.
CPC ........ *C07D 401/12* (2013.01); *C07B 2200/13* (2013.01)
(58) Field of Classification Search
CPC .................................................... C07D 401/12
USPC ........................................................ 546/273.4
See application file for complete search history.

(56) References Cited

FOREIGN PATENT DOCUMENTS

| CN | 102924434 A | 2/2013 |
|---|---|---|
| CN | 104031030 A | 9/2014 |
| CN | 104725358 A | 6/2015 |
| CN | 104910135 A | 9/2015 |

OTHER PUBLICATIONS

Nochi, Chem. Pharm. Bull. 44(10) 1853-1857 (1996).*
Sep. 28, 2018 Search Report issued in International Patent Application No. PCT/CN2018/092347.

* cited by examiner

*Primary Examiner* — Nizal S Chandrakumar
(74) *Attorney, Agent, or Firm* — Oliff PLC (57) ABSTRACT

A dexrabeprazole sodium compound includes crystal forms B and C. The crystal form B has good stability and flowability. The crystal form C is an anhydrous crystal form and has good stability and low hygroscopicity. The crystal forms are suitable for preparing a dexrabeprazole sodium preparation.

4 Claims, 8 Drawing Sheets

DEXRABEPRAZOLE SODIUM COMPOUND AND PHARMACEUTICAL COMPOSITION THEREOF

TECHNICAL FIELD

The present invention belongs to the medicine field, and in particular relates to new crystal forms of a dexrabeprazole sodium compound and a method for preparing the same, as well as a pharmaceutical composition containing the dexrabeprazole sodium compound.

BACKGROUND ART

Dexrabeprazole sodium (Formula I), with a chemical name of R-(+)-2-{[4-(3-methoxypropoxy)-3-methylpyrid-2-yl]methylsulfinyl}-1H-benzimidazole sodium salt, was first developed by Indian Emcure Pharmaceuticals, and listed in India in September, 2007. Dexrabeprazole sodium is used for the treatment of gastric ulcer, duodenal ulcer, stomal ulcer, reflux esophagitis, Zollinger-Ellisonsyndrome, (gastrinoma) active duodenal ulcer, benign active gastric ulcer, and erosive or ulcerative gastroesophageal reflux disease accompanied with clinical symptoms, and can effect a radical cure of *Helicobacter pylori*-positive duodenal ulcer when used in conjunction with proper antibiotic(s).

(I)

CN104910135A discloses an amorphous form of dexrabeprazole sodium, which has however poor stability and is not suitable for preparation of a solid preparation. CN102924434A discloses a monohydrate crystal form of dexrabeprazole sodium which is a relatively stable crystal form currently disclosed. In addition to the above, no other crystal forms of dexrabeprazole sodium are found. To improve the quality of dexrabeprazole sodium preparation, it is of significant importance to further research and develop an optimal drug crystal form of dexrabeprazole sodium.

SUMMARY OF THE INVENTION

An object of the present invention is to provide new crystal forms of dexrabeprazole sodium of Formula (I), and the new crystal forms have good stability, superior flowability, and low hygroscopicity, and are suitable for preparing pharmaceutical preparations, especially solid preparations.

(I)

In one aspect, the present invention provides a crystal form B of a dexrabeprazole sodium compound. As to the crystal form B, when measured by Cu target radiation, an X-ray powder diffraction (XRPD) pattern represented by angle 2θ has characteristic peaks at about 6.50±0.2°, 8.6±0.2°, 14.46±0.2°, 15.92±0.2°, 17.7±0.2°, 18.40±0.2°, 19.58±0.2°, and 23.46±0.2°. Wherein, the peak with the highest relative intensity is the characteristic peak at about 23.46±0.2°.

Further, the X-ray powder diffraction pattern has characteristic peaks at about 6.50±0.2°, 8.64±0.2°, 10.58±0.2°, 13.14±0.2°, 14.46±0.2°, 14.90±0.2°, 15.48±0.2°, 15.92±0.2°, 16.86±0.2°, 17.74±0.2°, 18.40±0.2°, 19.58±0.2°, 20.3±0.2°, 21.00±0.2°, 21.56±0.2°, 22.44±0.2°, 22.90±0.2°, 23.46±0.2°, and 24.04±0.2°.

Figure 1:
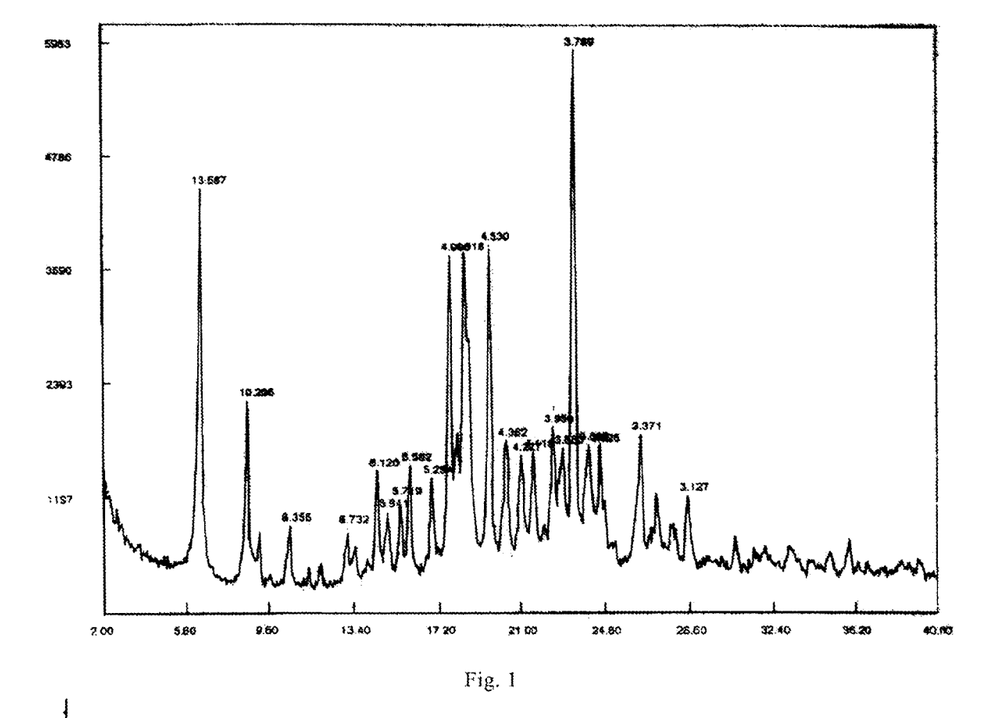
FIG. 1 is an XRPD pattern of a crystal form B of a dexrabeprazole sodium compound.

Further, the crystal form B of dexrabeprazole sodium has an XRPD pattern basically as shown in FIG. 1. Wherein, the angle 2θ allows an error of ±0.2°.

A differential scanning calorimetric (DSC) pattern of the crystal form B of dexrabeprazole sodium compound has an endothermic peak at about 138° C. and exothermic peaks at about 189° C. and about 226° C. Wherein, the temperature allows an error of ±5° C.

Figure 2:
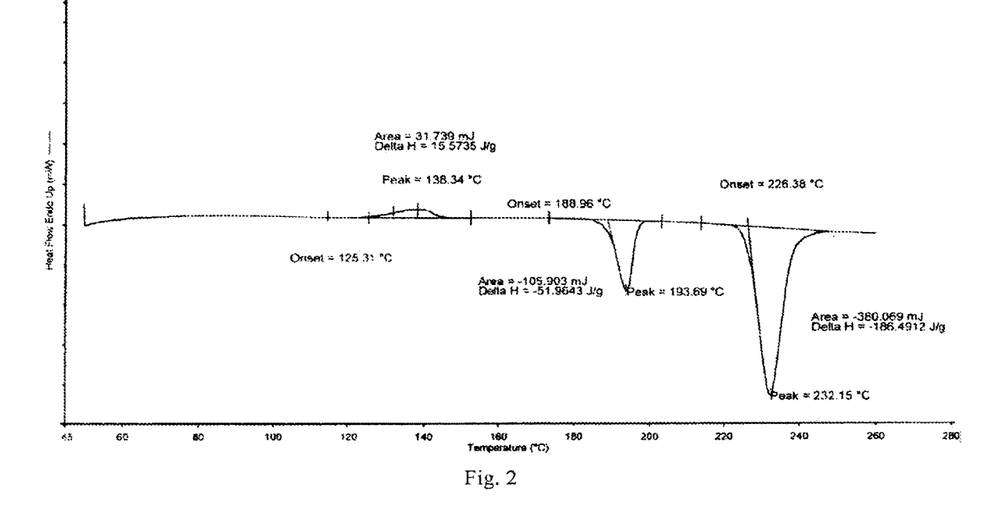
FIG. 2 is a DSC pattern of a crystal form B of a dexrabeprazole sodium compound.

The crystal form B of dexrabeprazole sodium compound has a DSC pattern basically as shown in FIG. 2.

Figure 3:
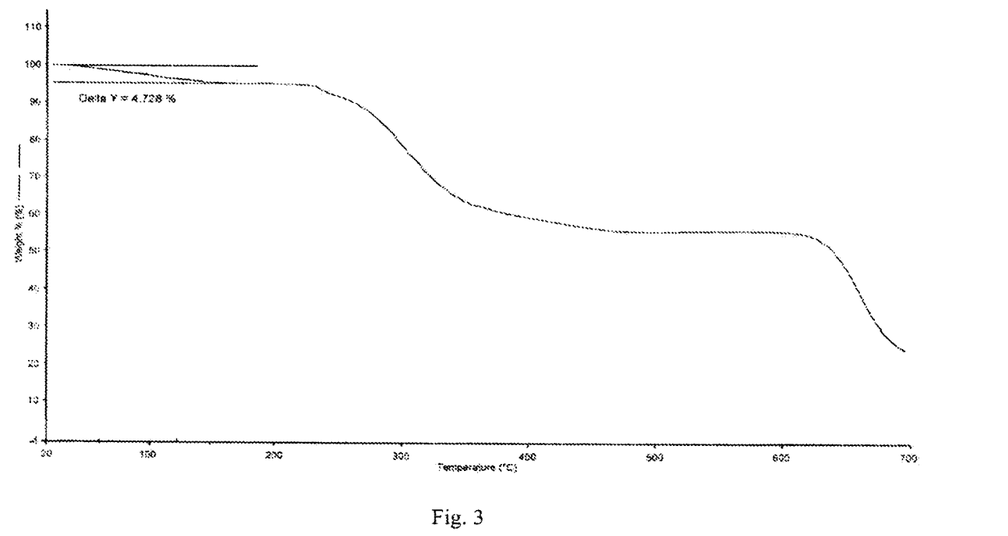
FIG. 3 is a TGA pattern of a crystal form B of a dexrabeprazole sodium compound.

The crystal form B of dexrabeprazole sodium compound has a Thermo gravimetric Analysis (TGA) pattern basically as shown in FIG. 3.

Figure 4:
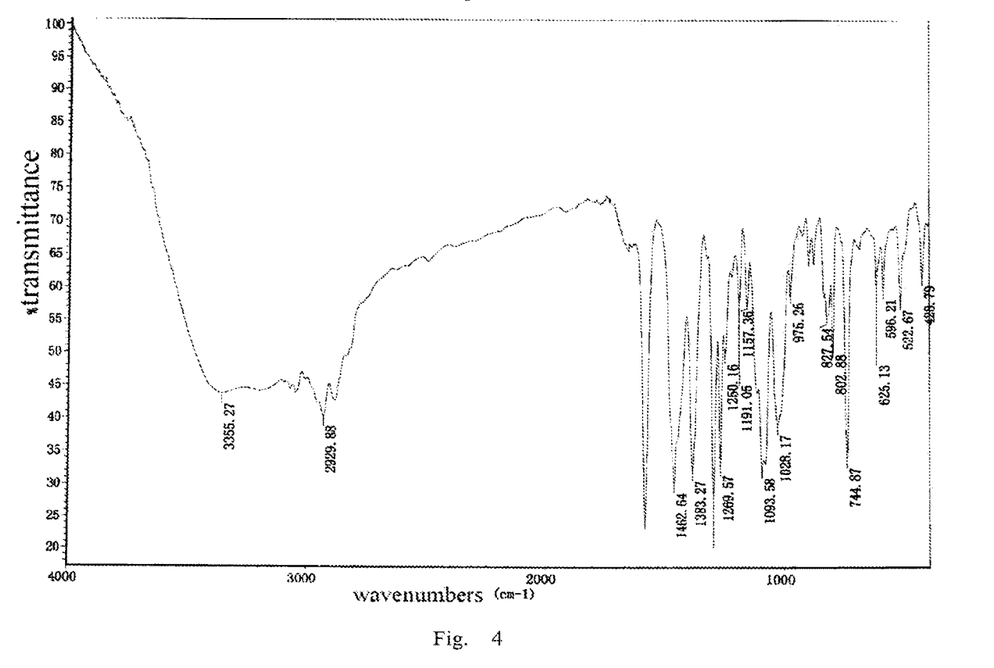
FIG. 4 is an IR spectrogram of a crystal form B of a dexrabeprazole sodium compound.

The crystal form B of dexrabeprazole sodium compound has an infrared (IR) spectrogram basically as shown in FIG. 4.

The present invention further provides a method for preparing the crystal form B of dexrabeprazole sodium compound of Formula (I), comprising:

1) adding dexrabeprazole to an organic solvent, stirring the mixture, separating an organic layer, and concentrating the organic layer to dryness;

2) adding an alcohol solvent and an aqueous solution of sodium hydroxide to the residue obtained in step 1, and stirring the mixture for reaction; and 3) after completion of reaction, adding dropwise an anti-solvent to the reaction mixture for crystallization to obtain the desired compound.

In step 1), the organic solvent is selected from a group consisting of dichloromethane, trichloromethane and ethyl acetate, preferably dichloromethane.

In step 2), the alcohol solvent is selected from a group consisting of isopropanol, n-propanol and n-butanol, preferably isopropanol.

In step 3), the anti-solvent is selected from a group consisting of isopropyl ether, methyl tert-butyl ether, diethyl ether and methyl ethyl ether, preferably isopropyl ether.

In a preferred embodiment, the ratio of dexrabeprazole to the organic solvent in step 1) can be 1 g:(1-10) ml, e.g., 1 g:(3-5) ml.

In a preferred embodiment, the ratio of dexrabeprazole to the alcohol solvent in step 2) can be 1 g:(1-10) ml, e.g., 1 g:(3-5) ml.

In a preferred embodiment, the aqueous solution of sodium hydroxide in step 2) has a concentration of 40 wt %.

In a preferred embodiment, the amount of the anti-solvent in step 3) is one to five times the volume of the reaction mixture, for example, 2-3 times.

In a preferred embodiment, in step 3), after completion of reaction, the reaction mixture can be concentrated to reduce the volume thereof, and then the anti-solvent is added dropwise.

Concentration refers to reduction of the solution to any volume, such as, ½ volume, ⅓ volume, ¼ volume, ⅕ volume, and the like. After concentration of the reaction mixture, the anti-solvent is added dropwise for crystallization, therefore, the amount of the anti-solvent can be correspondingly reduced, and the crystallization process is accelerated. The concentration can be in a range of 35 to 45° C.

In a preferred embodiment, the dropwise addition of the anti-solvent in step 3) can be performed at a low temperature, and the low temperature can be 10° C. or below. For instance, the reaction mixture is cooled to 0 to 10° C., preferably 0 to 5° C., and then the anti-solvent is added dropwise for crystallization.

In another aspect, the present invention provides a crystal form C of a dexrabeprazole sodium compound. As to the crystal form C, when measured by Cu target radiation, an X-ray powder diffraction (XRPD) pattern represented by angle 2θ has characteristic peaks at about 6.22±0.2°, 12.14±0.2°, 12.46±0.2°, 15.82±0.2°, 18.90±0.2°, 22.38±0.2°, 26.56±0.2°, and 28.06±0.2°. Wherein, the peak with the highest relative intensity is the characteristic peak at about 6.22±0.2°.

Further, the X-ray powder diffraction pattern has characteristic peaks at about 6.22±0.2°, 12.14±0.2°, 12.46±0.2°, 13.10±0.2°, 15.82±0.2°, 17.34±0.2°, 17.70±0.2°, 18.90±0.2°, 20.18±0.2°, 20.74±0.2°, 21.60±0.2°, 22.08±0.2°, 22.38±0.2°, 23.42±0.2°, 26.56±0.2°, 28.06±0.2°, and 30.80±0.2°.

Figure 6:
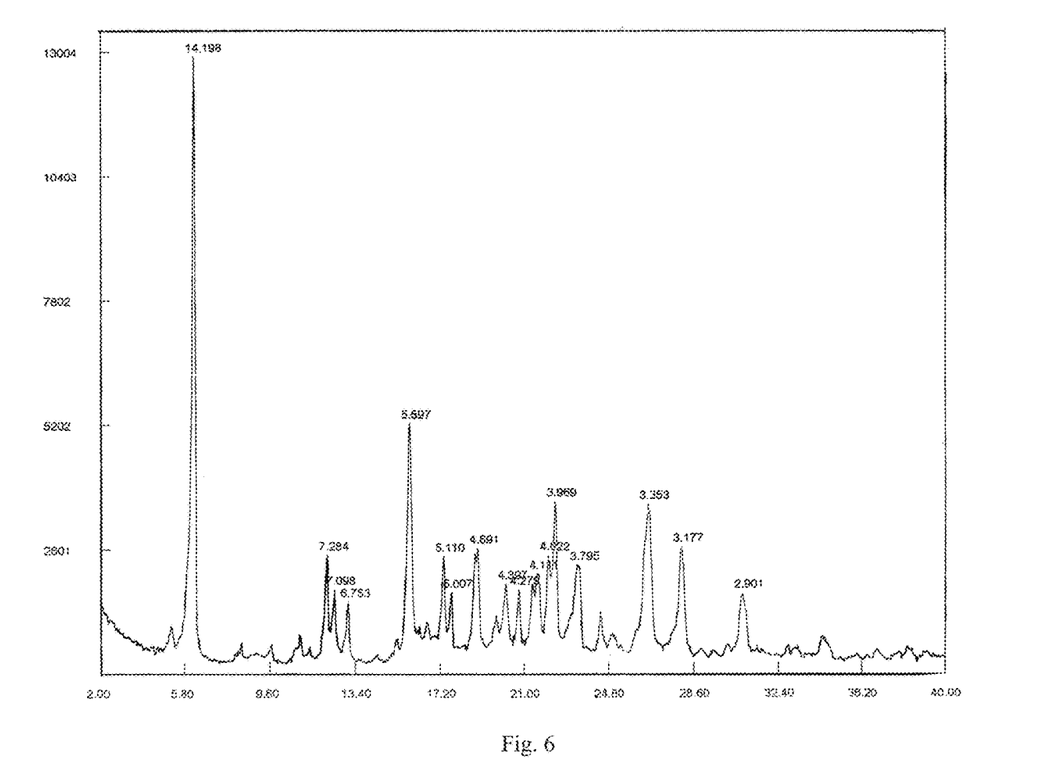
FIG. 6 is an XRPD pattern of a crystal form C of a dexrabeprazole sodium compound.

Further, the crystal form C of a dexrabeprazole sodium compound has an XRPD pattern basically as shown in FIG. 6. Wherein, the angle 2θ allows an error of ±0.2°. A differential scanning calorimetric (DSC) pattern of the crystal form C of a dexrabeprazole sodium compound has an exothermic peak at about 234° C. Wherein, the temperature allows an error of ±5° C.

Figure 7:
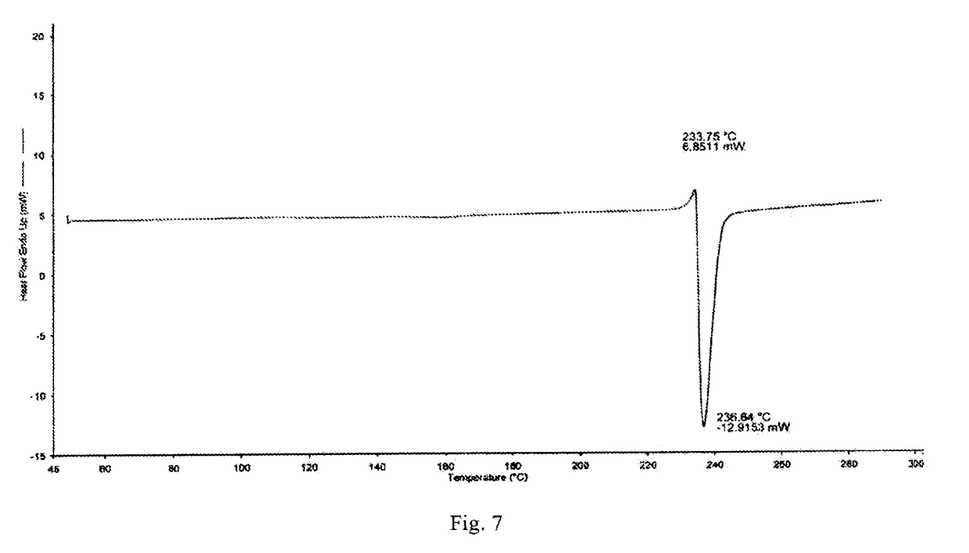
FIG. 7 is a DSC pattern of a crystal form C of a dexrabeprazole sodium compound.

The crystal form C of a dexrabeprazole sodium compound has a DSC pattern basically as shown in FIG. 7.

Figure 8:
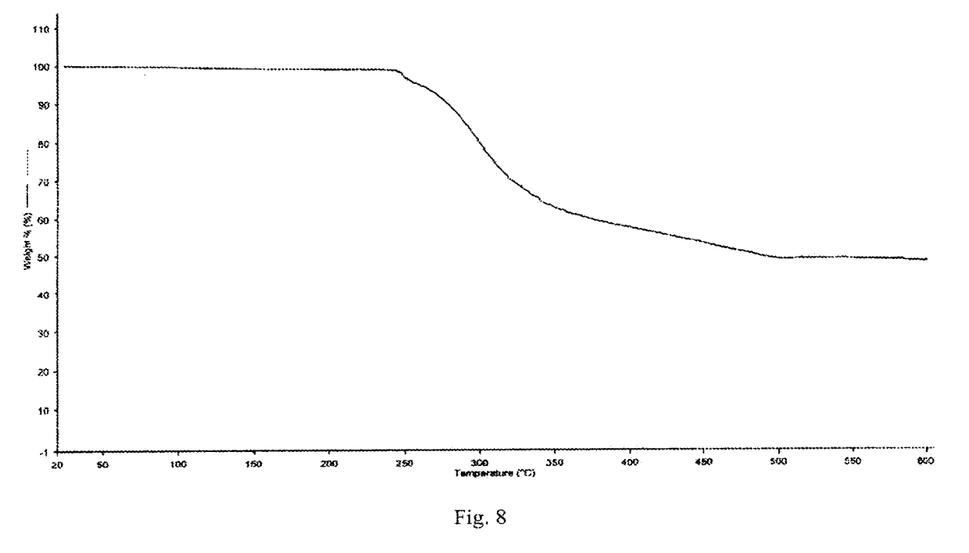
FIG. 8 is a TGA pattern of a crystal form C of a dexrabeprazole sodium compound.

The crystal form C of a dexrabeprazole sodium compound has a TGA pattern basically as shown in FIG. 8.

Figure 9:
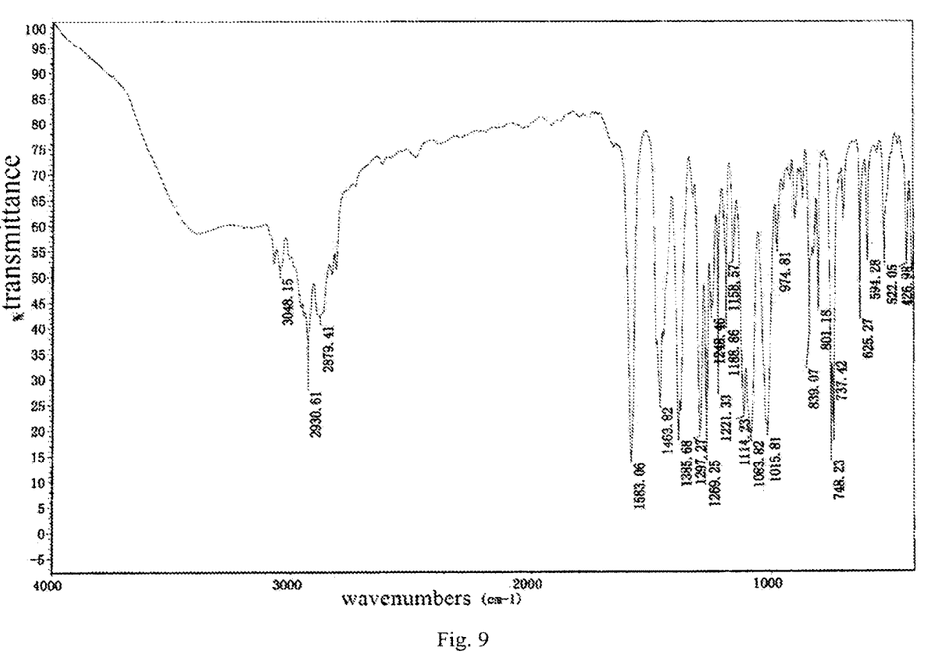
FIG. 9 is an IR spectrogram of a crystal form C of a dexrabeprazole sodium compound.

The crystal form C of a dexrabeprazole sodium compound has an IR spectrogram basically as shown in FIG. 9.

The present invention further provides a method for preparing the crystal form C of a dexrabeprazole sodium compound of Formula (I), comprising the following steps:

1) dissolving dexrabeprazole sodium in methanol or ethanol, concentrating the mixture to dryness under reduced pressure, and repeating the foregoing operation at least once;

2) adding acetonitrile to the residue obtained in step 1), stirring and concentrating the mixture to dryness under reduced pressure; and 3) adding a solvent toluene or xylene to the residue obtained in step 2), and stirring the mixture for crystallization to obtain the crystal form C.

In a preferred embodiment, in step 1), the dexrabeprazole sodium is dissolved in methanol.

In a preferred embodiment, in step 1), the operation of dissolution and concentration is preferably repeated for one to six times, more preferably 2-5 times, e.g., 3-4 times.

In a preferred embodiment, in step 3), the stirring for crystallization is performed under inert gas protection, e.g., nitrogen.

In a preferred embodiment, the ratio of dexrabeprazole sodium to the organic solvent in step 1) can be 1 g:(1-20) ml, e.g., 1 g:(3-10) ml.

In a preferred embodiment, the ratio of dexrabeprazole sodium to the acetonitrile in step 2) can be 1 g:(1-20) ml, e.g., 1 g:(3-10) ml.

In a preferred embodiment, the ratio of dexrabeprazole sodium to the solvent in step 3) can be 1 g:(5-30) ml.

The present invention further provides a pharmaceutical composition which contains the aforesaid crystal forms of dexrabeprazole sodium compound and a pharmaceutically acceptable carrier. The pharmaceutical composition can be prepared into any dosage form, preferably oral preparations, e.g., enteric-coated tablets, capsules, etc.; or injectable preparations, e.g., freeze-dried powder injection.

The present invention further provides applications of the foregoing dexrabeprazole sodium compound or a pharmaceutical composition thereof in preparation of a drug for treatment or prevention of gastrointestinal diseases. For example, the drug can be used for treating or preventing, e.g., gastric ulcer, duodenal ulcer, stomal ulcer, reflux esophagitis, Zollinger-Ellisonsyndrome (gastrinoma), active duodenal ulcer, benign active gastric ulcer, erosive or ulcerative gastroesophageal reflux diseases accompanied with clinical symptoms, and can effect a radical cure of *Helicobacter pylori*-positive duodenal ulcer when used in conjunction with proper antibiotic(s).

The crystal form B of dexrabeprazole sodium of the present invention shows good stability, has good flowability, and is especially suitable for preparing oral preparations, as it can improve the uniformity and quality stability of preparations. The crystal form C of dexrabeprazole sodium of the present invention is an anhydrous crystal form, which is low in moisture and poor in hydroscopicity. Thus, the crystal form C has good stability and is suitable for preparation of a drug preparation.

DETAILED DESCRIPTION OF THE EMBODIMENTS

The present invention is described in detail below through particular examples. However, those skilled in the art can understand that the following examples are merely for an illustrative purpose, rather than for limiting the scope of the present invention in any way. Unless otherwise specified, all the operation steps in the examples are conventional operations.

Test Methods:

XRPD test (FIGS. 1&6, Testing & Analysis Center, Nanjing Normal University): Instrument model: D/max2500VL/PC, target: Cu (60 kV, 100 mA), scanning range: 3°-40° (2θvalue), scanning step length: 0.02, scanning speed: 5.

DSC test: Instrument model: PerkinElmer DSC 8500, temperature range: 50-300° C., scanning speed: 10° C./min, $N_2$ flowrate: 50 ml/min.

TGA test: Instrument model: Netzsch TG209F3, temperature range: 25-700° C., scanning speed: 20° C./min, purge gas: 25 ml/min, protective gas: 15 ml/min.

IR test: Thermo Co., Ltd., Instrument model: NICOLE-Tis5 Infrared Chromatographic Instrument, scanning times: 32, DPI: 4.000, sampling gain: 1.0, movement speed: 0.4747, diaphragm: 100.00, detector: DTGSKBr, beam spliter: KBr, light source: infrared light source.

XRPD test (FIGS. 10 & 12-14, Modern Analysis Center, Nanjing University): Instrument model: Thermo Co., Ltd., X'TRA Type X Diffractometer, target: Cu (40 kV, 40 mA), scanning range: 2°-40° (2θvalue), scanning step length: 0.02, scanning speed: 5

SEM scanning: S-3400N, EX-250 electron microscope

Determination of angle of repose: BT-1001 Intelligent Powder Characteristic Tester (Dandong Bettersize Instrument Co., Ltd.)

Determination of hygroscopic moisture: 25±1° C. Thermostatic Drier (with a saturated solution of ammonium chloride being placed at bottom of the drier).

Chromatographic conditions of relevant materials:

Chromatographic column: charged with octadecylsilane bonded silica as a filler (Agilent ZORBAX Extend C18, 250×4.6 mm, 5 nm);

Mobile phase A: 0.025 mol/L of phosphate solution (the pH of 0.025 mol/L of dipotassium phosphate solution was adjusted to 7.2 with phosphoric acid)-acetonitrile (95:5); Mobile phase B: methanol; Mobile phase C: acetonitrile;

A linear gradient elution is carried out in accordance with the following table.

| Time (min) | A (%) | B (%) | C (%) |
|---|---|---|---|
| 0 | 65 | 30 | 5 |
| 15 | 65 | 30 | 5 |
| 45 | 15 | 55 | 30 |
| 50 | 15 | 55 | 30 |
| 52 | 65 | 30 | 5 |
| 60 | 65 | 30 | 5 |

Detection wavelength: 280 nm, 220 nm (for impurity H)
Flowrate: 1.0 ml/min
Column temperature: 25° C.
Sample size: 5 μl
Diluent: the pH of 0.1 mol/L of dipotassium phosphate solution was adjusted to 11.3 with 2 mol/L potassium hydroxide solution-methanol (45:55).

Chromatographic conditions for detection of laevo isomer:

Chromatographic column: Chiralpack AGP Chiral Chromatographic Column (150 mm×4.0 mm, 5 μm)

Mobile phase: 0.01 mol/L of phosphate solution (the pH of 0.01 mol/L of dipotassium phosphate solution was adjusted to 6.8 with phosphoric acid)-acetonitrile (90:10)

Diluent: 0.05 mol/L of sodium hydroxide solution-methanol (40:60)

Detection wavelength: 290 nm

Flowrate: 0.8 ml/min

Column temperature: 30° C.

Sample size: 10 μl

Example 1: Preparation of Crystal Form B of Dexrabeprazole Sodium

Dichloromethane (75 ml) was added to wet dexrabeprazole (25.12 g). The mixture was stirred thoroughly, and stood for liquid separation. The upper aqueous phase was removed and weighed to be 8.98 g, and then the weight of dexrabeprazole was about 16.14 g. The dichloromethane phase was concentrated under reduced pressure at 30° C. to brown foam. Isopropanol (120 ml) and 40% aqueous solution of sodium hydroxide (1.98 g NaOH, 1.1 equivalent) were added to the residue, and reacted at 35° C. under stirring for 5 to 6 h. After completion of reaction, 1 ml of purified water was added to the reaction mixture, and stirred under nitrogen protection for 96 h. The reaction mixture was concentrated under reduced pressure at 45° C. to ½ volume, and cooled to 0 to 5° C. Isopropyl ether (60 ml) was added dropwise, stirred for 4 to 5 h, and filtered. The filter cake was rinsed with isopropyl ether (50 ml) and drained, and dried under reduced pressure to obtain white solids (14.37 g). The moisture was measured to be 4.72%, HPLC was 99.91%, and isomer HPLC was 100%.

Figure 5:
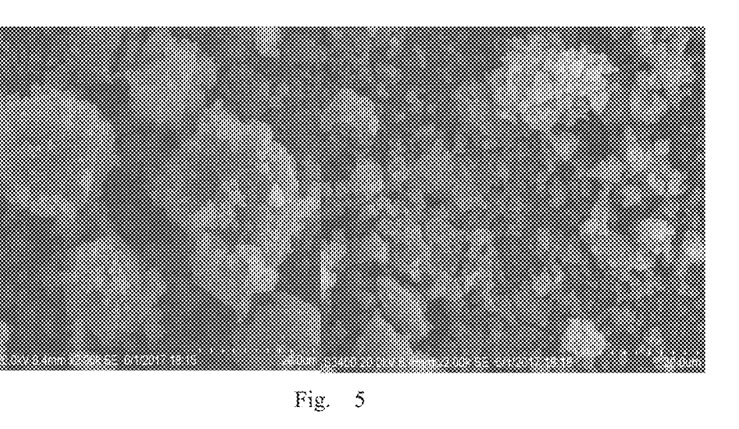
FIG. 5 is an SEM photograph of a crystal form B of a dexrabeprazole sodium compound.

The XRPD pattern is as shown in FIG. 1. The DSC pattern is as shown in FIG. 2, and shows a wide endothermic peak at about 138° C. and exothermic peaks at about 189° C. and 226° C., respectively. The TGA pattern is as shown in FIG. 3. The IR spectrogram is as shown in FIG. 4. The SEM photograph is as shown in FIG. 5.

TABLE 1

XRPD Pattern Data of Crystal Form B of Dexrabeprazole Sodium

| No. | 2θ | d value | Relative intensity |
|---|---|---|---|
| 1 | 6.50 | 13.587 | 75 |
| 2 | 8.64 | 10.226 | 37 |
| 3 | 10.58 | 8.355 | 15 |
| 4 | 13.14 | 6.732 | 15 |
| 5 | 14.46 | 6.12 | 24 |
| 6 | 14.90 | 5.941 | 18 |
| 7 | 15.48 | 5.719 | 20 |
| 8 | 15.92 | 5.562 | 25 |
| 9 | 16.86 | 5.254 | 23 |
| 10 | 17.74 | 4.996 | 63 |
| 11 | 18.40 | 4.818 | 63 |
| 12 | 19.58 | 4.530 | 65 |
| 13 | 20.34 | 4.362 | 30 |
| 14 | 21.00 | 4.227 | 27 |
| 15 | 21.56 | 4.118 | 28 |
| 16 | 22.44 | 3.959 | 32 |
| 17 | 22.90 | 3.880 | 29 |
| 18 | 23.46 | 3.789 | 100 |
| 19 | 24.04 | 3.699 | 29 |
| 20 | 24.54 | 3.625 | 29 |
| 21 | 26.42 | 3.371 | 31 |
| 22 | 28.52 | 3.127 | 20 |

Example 2: Preparation of Crystal Form B of Dexrabeprazole Sodium

Dichloromethane (750 ml) was added to wet dexrabeprazole (250 g). The mixture was stirred thoroughly, and stood for liquid separation. The upper aqueous phase was removed and weighed to be 88.96 g, and then the weight of dexrabeprazole was about 161.04 g. The dichloromethane phase was concentrated under reduced pressure at 30° C. to foam. Isopropanol (1200 ml) and 40% aqueous solution of sodium hydroxide (20 g NaOH, 1.1 equivalent) were added to the residue, reacted at 35° C. under stirring for 6 h. After completion of reaction, the reaction mixture was concentrated under reduced pressure at 45° C. to ⅓ volume, and cooled to 0 to 5° C. Isopropyl ether (620 ml) was added dropwise, stirred for 5 h, and filtered. The filter cake was rinsed with isopropyl ether (500 ml) and drained, and dried under reduced pressure to obtain white solids (145.12 g). The test pattern is consistent with that of Example 1.

Example 3: Preparation of Crystal Form B of Dexrabeprazole Sodium

Trichloromethane (150 ml) was added to wet dexrabeprazole (50.55 g). The reaction mixture was stirred thoroughly, and stood for liquid separation. The upper aqueous phase was removed and weighed to be 18.65 g, and then the weight of dexrabeprazole was about 31.90 g. The trichloromethane phase was concentrated under reduced pressure at 30° C. to foam. Isopropanol (240 ml) and 40% aqueous solution of sodium hydroxide (4.0 g NaOH, 1.1 equivalent) were added to the residue, reacted at 35° C. under stirring for 5 to 6 h. After completion of reaction, the reaction mixture was concentrated under reduced pressure at 45° C. to ½ volume, and cooled to 0 to 5° C. Methyl tert-butyl ether (150 ml) was added dropwise, stirred for 4 to 5 h, and filtered. The filter cake was rinsed with methyl tert-butyl ether (80 ml) and drained, and dried under reduced pressure to obtain white solids (28.38 g). The test pattern is consistent with that of Example 1.

Example 4: Preparation of Crystal Form C of Dexrabeprazole Sodium

Methanol (50 ml) was added to dexrabeprazole sodium (10 g), and stirred to dissolve. The mixture was concentrated under reduced pressure at 45° C. to dryness, to show a shape of foam. The foregoing concentration step was repeated for 5 times. Acetonitrile (50 ml) was added to the residue, stirred at about 20-35° C., and crystallized for 18-24 h. The reaction mixture was concentrated under reduced pressure at a temperature of 45° C. Toluene (150 ml) was added to the residue, stirred at 35° C. under nitrogen protection, crystallized for 24 h, and filtered. The filter cake was rinsed with toluene (50 ml) and drained, and dried under reduced pressure at 40° C. for 24 h to obtain white solids (9.5 g). Relevant materials HPLC: 99.92%, individual impurity: 0.028%, moisture KF: 0.11%; isomer HPLC: 100%.

The XRPD pattern is as shown in FIG. 6. The DSC pattern is as shown in FIG. 7. The TGA pattern is as shown in FIG. 8. The IR spectrogram is as shown in FIG. 9.

TABLE 2

XRPD Pattern Data of Crystal Form C of Dexrabeprazole Sodium

| No. | 2θ | d value | Relative intensity |
|---|---|---|---|
| 1 | 6.22 | 14.198 | 100 |
| 2 | 12.14 | 7.284 | 19 |
| 3 | 12.46 | 7.098 | 13 |
| 4 | 13.10 | 6.753 | 11 |
| 5 | 15.82 | 5.597 | 40 |
| 6 | 17.34 | 5.110 | 19 |
| 7 | 17.70 | 5.007 | 13 |
| 8 | 18.90 | 4.691 | 20 |
| 9 | 20.18 | 4.397 | 14 |
| 10 | 20.74 | 4.279 | 13 |
| 11 | 21.60 | 4.111 | 16 |
| 12 | 22.08 | 4.022 | 19 |
| 13 | 22.38 | 3.969 | 27 |
| 14 | 23.42 | 3.795 | 17 |
| 15 | 26.56 | 3.353 | 27 |
| 16 | 28.06 | 3.177 | 20 |
| 17 | 30.80 | 2.901 | 13 |
| — | — | — | — |

Example 5: Preparation of Crystal Form C of Dexrabeprazole Sodium

Methanol (100 ml) was added to dexrabeprazole sodium (20 g), and stirred to dissolve. The mixture was concentrated under reduced pressure at 45° C. to dryness, to show a shape of foam. The aforesaid concentration step was repeated for four times. Acetonitrile (100 ml) was added to the residue at about 25° C., stirred, and crystallized for 20 h. The reaction mixture was concentrated under reduced pressure at 45° C. Toluene (300 ml) was added to the residue, stirred under nitrogen protection at 35° C., crystallized for 24 h, and filtered. The filter cake was rinsed with toluene (90 ml) and drained, and dried under reduced pressure at 40° C. for 24 h to obtain white solids (18.9 g). The test pattern is basically consistent with that of Example 1.

Figure 10:
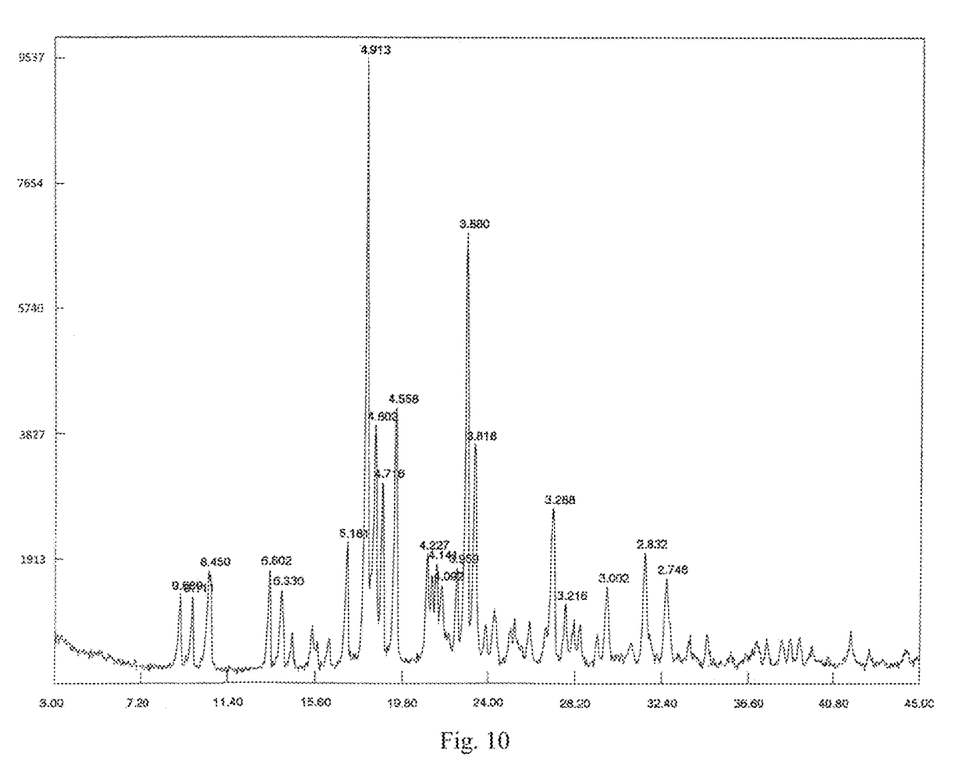
FIG. 10 is an XRPD pattern of a crystal form A of a dexrabeprazole sodium compound.
Figure 11:
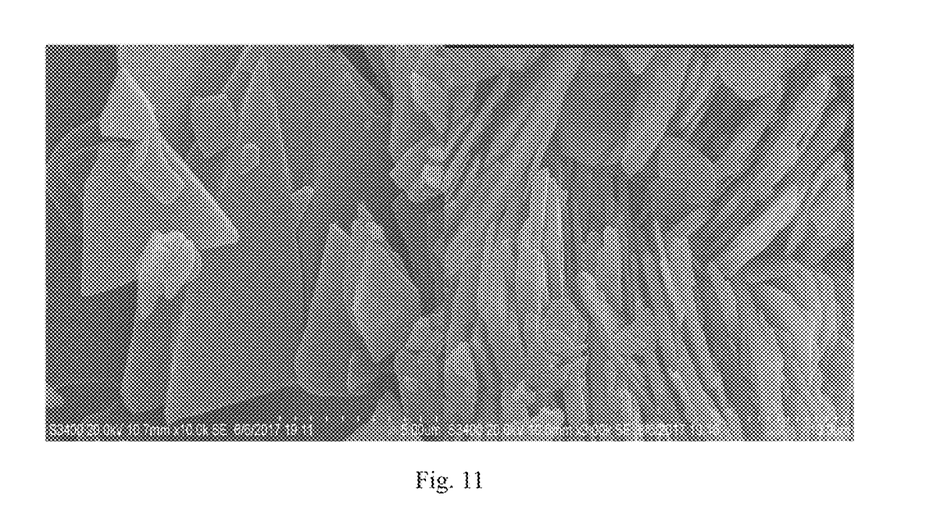
FIG. 11 is an SEM photograph of a crystal form A of a dexrabeprazole sodium compound.

Example 6: Study on Physicochemical Properties of Various Crystal Forms of Dexrabeprazole Sodium Dexrabeprazole sodium crystal was prepared in accordance with the method of Example 1 in description of CN102924434A, and designated as crystal form A. The XRPD pattern is as shown in FIG. 10, and consistent with that of the above application. The SEM photograph is shown in FIG. 11.

Figure 12:
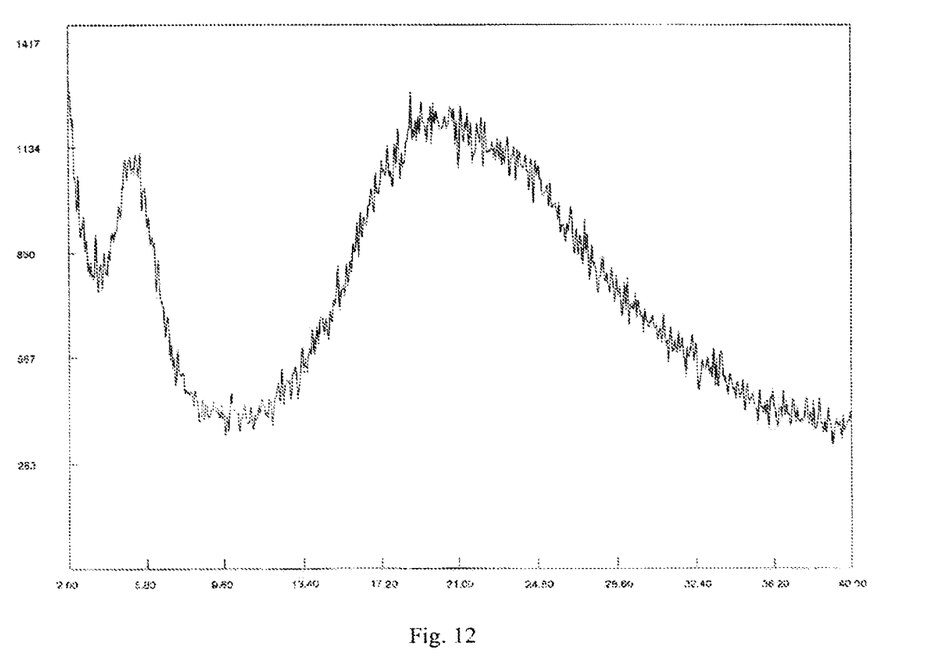
FIG. 12 is an XRPD pattern of an amorphous state of a dexrabeprazole sodium compound.

Dexrabeprazole (100 g) was dissolved in dichloromethane (300 ml). After phase separation, the upper aqueous layer was removed. Isopropyl ether (2 L) was slowly added to the organic layer, stirred at room temperature for 1 h, and filtered. The filter cake was rinsed with isopropyl ether (500 ml) and drained, and dried under reduced pressure at 35° C. for 12 h to obtain dexrabeprazole sodium solid (63.5 g), which was an amorphous solid. The XRPD pattern is as shown in FIG. 12.

The aforesaid amorphous form, and crystal forms A, B, and C of dexrabeprazole sodium were sampled, respectively, and detected for their physicochemical properties. The results are listed in Table 3.

TABLE 3

Study of Physicochemical Properties of Various Crystal Forms of Dexrabeprazole Sodium

| Form | Melting point (° C.) | | | Solulibity in water | Character of appearance | Hygroscopic moisture (%) | | |
|---|---|---|---|---|---|---|---|---|
| | Initial melting | Full melting | Melting range | | | 0 h | 24 h | 48 h |
| Amorphous form | 46.41 | 57.55 | 46.41-57.55 | Soluble | Off-white powders | 6.60 | 21.60 | 21.81 |
| Crystal form A | 191.03 | 191.12 | 191.03-191.12 | Soluble | Off-white powders | 4.66 | 5.10 | 5.72 |
| Crystal form B | 147.41 | 147.61 | 147.41-147.61 | Soluble | Off-white powders | 4.72 | 5.18 | 5.75 |
| Crystal form C | 222.24 | 222.52 | 222.24-222.52 | Soluble | Off-white powders | 0.11 | 0.15 | 0.18 |

Testing results show that the appearance characters of four samples are all off-white powders. The amorphous form has a relatively low melting point and a relatively long melting range, and is in a thermodynamically unstable state. All the crystal forms have a relatively high melting point, wherein the melting point of crystal form C is significantly higher than that of crystal A. Solubilities in water basically have no differences, which are all "soluble". The measurement of hygroscopic moisture after 24 h and 48 h indicates that the amorphous form has the highest hygroscopic moisture, and crystal form A and crystal form B are comparable in terms of hygroscopic moisture. From the results of investigation on hygroscopic moisture, it is unexpectedly found that the hygroscopic moisture of crystal form C is lower than that of crystal form A. Moreover, due to the extremely low initial moisture of crystal form C (almost anhydrous), it has a potential advantage of maintaining a relatively low moisture content for a long term during storage. Especially during the storage of, e.g., oral tablets, capsules, or the like, low moisture content and anti-moisture absorption can often increase chemical stability of the APIs and the adjuvants, thereby effectively reducing the degradation side reactions of the APIs and the adjuvants due to excessive moisture absorption, and avoiding the reduction of in vivo disintegration performance caused by excessive moisture of the product and early contact of the disintegrating agent with the moisture.

Example 7: Study of Stability of Various Crystal Forms of Dexrabeprazole Sodium 7.1 Test of Influence Factors Crystal forms A, B, and C (each 100 mg) were placed under different conditions, and sampled at Days 0, 10, 20, and 30 for detecting their characters and relevant materials, respectively. The results are listed in Table 4.

TABLE 4

Study of Stability of Various Crystal Forms of Dexrabeprazole Sodium

| Crystal form | Conditions of influence factors | Time | Appearance character | Maximum individual impurity (%) | Total impurity (%) |
|---|---|---|---|---|---|
| Crystal form A | High temperature, 40° C. | Day 0 | Off-white powders | 0.037 | 0.098 |
| | | Day 10 | Off-white powders | 0.037 | 0.100 |
| | | Day 20 | Off-white powders | 0.021 | 0.145 |
| | | Day 30 | Off-white powders | 0.019 | 0.210 |
| | High humidity, RH75 ± 5% | Day 0 | Off-white powders | 0.037 | 0.098 |
| | | Day 10 | Yellow powders | 0.029 | 0.152 |
| | | Day 20 | Yellow powders | 0.200 | 0.483 |
| | | Day 30 | Yellow powders | 0.287 | 1.495 |
| | Light exposure, 4500 ± 500 Lx | Day 0 | Off-white powders | 0.037 | 0.098 |
| | | Day 10 | Off-white powders | 0.077 | 0.133 |
| | | Day 20 | Off-white powders | 0.099 | 0.298 |
| | | Day 30 | Off-white powders | 0.123 | 0.396 |
| Crystal form B | High temperature, 40° C. | Day 0 | Off-white powders | 0.029 | 0.088 |
| | | Day 10 | Off-white powders | 0.028 | 0.090 |
| | | Day 20 | Off-white powders | 0.015 | 0.126 |
| | | Day 30 | Off-white powders | 0.012 | 0.190 |
| | High humidity, RH75 ± 5% | Day 0 | Off-white powders | 0.029 | 0.088 |
| | | Day 10 | Yellow powders | 0.017 | 0.141 |
| | | Day 20 | Yellow powders | 0.189 | 0.426 |
| | | Day 30 | Yellow powders | 0.280 | 1.300 |
| | Light exposure 4500 ± 500 Lx | Day 0 | Off-white powders | 0.029 | 0.088 |
| | | Day 10 | Off-white powders | 0.059 | 0.120 |
| | | Day 20 | Off-white powders | 0.155 | 0.263 |
| | | Day 30 | Off-white powders | 0.100 | 0.360 |
| Crystal form C | High temperature, | Day 0 | Off-white powders | 0.032 | 0.085 |

TABLE 4-continued

Study of Stability of Various Crystal Forms of Dexrabeprazole Sodium

| Crystal form | Conditions of influence factors | Time | Appearance character | Relevant materials Maximum individual impurity (%) | Total impurity (%) |
|---|---|---|---|---|---|
| | 40° C. | Day 10 | Off-white powders | 0.030 | 0.093 |
| | | Day 20 | Off-white powders | 0.028 | 0.117 |
| | | Day 30 | Off-white powders | 0.024 | 0.136 |
| | High humidity RH75 ± 5% | Day 0 | Off-white powders | 0.032 | 0.085 |
| | | Day 10 | Off-white powders | 0.027 | 0.094 |
| | | Day 20 | Off-white powders | 0.015 | 0.166 |
| | | Day 30 | Off-white powders | 0.292 | 0.491 |
| | Light exposure 4500 ± 500 Lx | Day 0 | Off-white powders | 0.032 | 0.085 |
| | | Day 10 | Off-white powders | 0.088 | 0.112 |
| | | Day 20 | Off-white powders | 0.094 | 0.245 |
| | | Day 30 | Off-white powders | 0.113 | 0.344 |

Testing results show that, under conditions of light exposure, high temperature, and high humidity, the stability of crystal form B is comparable to that of crystal form A; under the condition of light exposure, the stability of crystal form C is comparable to that of crystal form A; and under the conditions of high temperature and high humidity, the stability of crystal form C is better than that of crystal form A.

7.2 High Temperature Test

Figure 13:
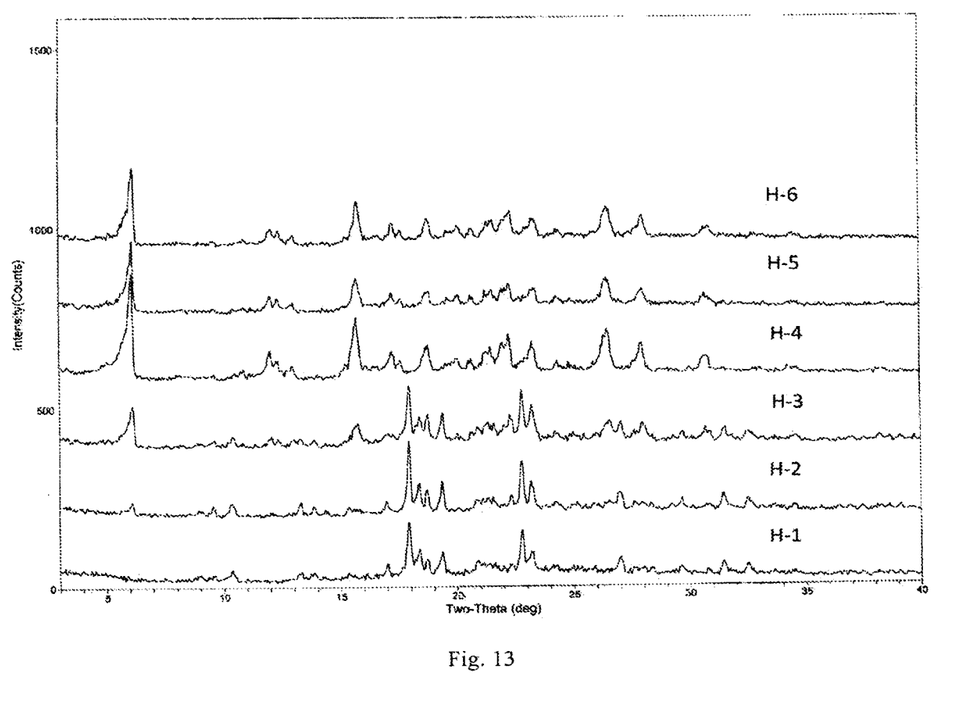
FIG. 13 is an XRPD pattern of various crystal forms of a dexrabeprazole sodium compound under grinding/high temperature conditions.

Crystal forms A and C of dexrabeprazole sodium were placed under different conditions as listed in Table 5 below, and sampled for XRPD detection to investigate the change of crystal forms. The XRPD fit chart is as shown in FIG. 13.

TABLE 5

Study of Stability of Various Crystal Forms of Dexrabeprazole Sodium at High Temperature

| Group | Conditions | Comparison of XRPD fit charts |
|---|---|---|
| H-1 | Crystal form A was grinded in a mortar for 5 min | Crystal form A was converted to partially amorphous |
| H-2 | Crystal form A was heated and dried at 80° C. for 2 h | Crystal form A was converted to partial crystal form C |
| H-3 | Crystal form A was heated and dried at 100° C. for 2 h | Crystal form A was converted to a higher proportion of crystal form C |
| H-4 | Heated and dried at 50° C. for 2 h | No crystal form C was converted |
| H-5 | Heated and dried at 80° C. for 2 h | |
| H-6 | Heated and dried at 100° C. for 2 h | |

Testing results show that, crystal form C keeps stable at a high temperature without crystal transformation; crystal form A is unstable at a high temperature, is prone to crystal transformation, and shows characteristic peaks of crystal form C, and thus it is estimated that crystal form A is converted to crystal form C at high temperature; and crystal form A is partially converted to an amorphous form upon grinding. Thus, crystal form C is the most stable crystal form, and is suitable for preparing solid preparations, such as, oral tablets, capsules, and the like.

7.3 Test of Suspension Equilibrium

Figure 14:
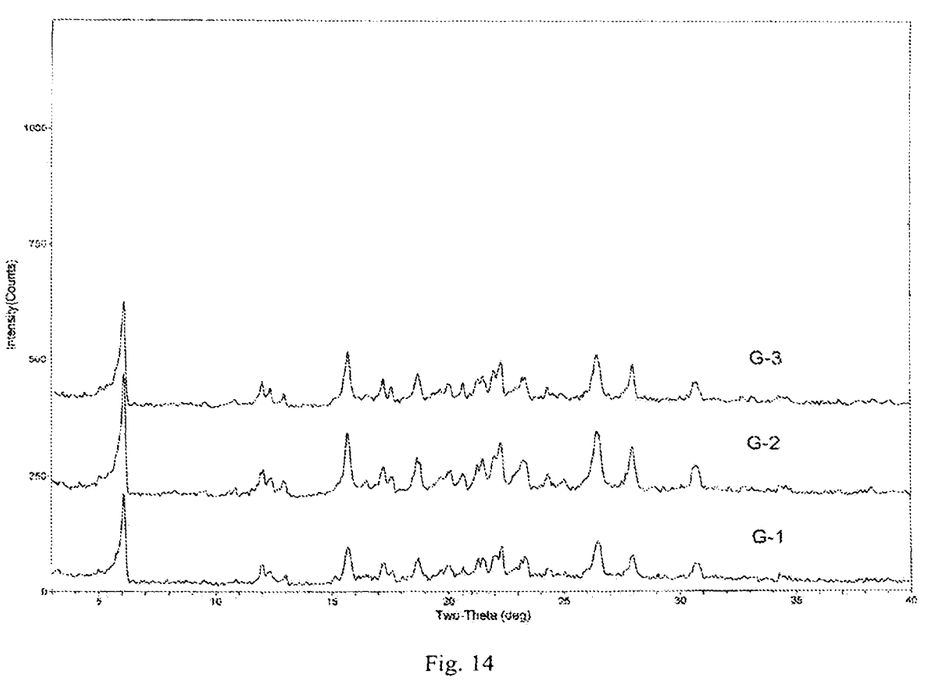
FIG. 14 is an XRPD pattern of various crystal forms of a dexrabeprazole sodium compound in a suspension solution.

Samples of amorphous form, crystal form A, and crystal form C (each 1 g) were mixed in accordance with the grouping in the table below. The mixture was stirred, together with 10 ml of a solvent at 35° C. and under nitrogen atmosphere, and then sampled for XRPD detection. The pattern is as shown in FIG. 14. The conditions and results of test are listed in Table 6 below.

TABLE 6

Suspension Equilibrium of Various Crystal Forms of Dexrabeprazole Sodium

| Group | Initial sample mixture | Suspension solvent | Suspension time(Day) | Crystal form of product |
|---|---|---|---|---|
| G-1 | Crystal form C + amorphous | Acetonitrile | 2 | Crystal form C |
| G-2 | Crystal form A + crystal form C | Acetonitrile | 2 | Crystal form C |
| G-3 | Crystal form A + amorphous | Acetonitrile | 2 | Crystal form C |

Results show that the crystal form C of dexrabeprazole sodium has better stability than amorphous form and crystal form A, and is a highly stable crystal form.

Example 8: Difference of Powder Flowability of Various Crystal Forms of Dexrabeprazole Sodium and Influence on Preparations 8.1 Fluidity Angle of repose is a key characteristic of the frictional resistance between powder particles, and is an important parameter for characterizing the powder flowability. The angle of repose is determined by measuring the height and the base radius of a cone formed by powders, with a calculation equation as follows: $\tan(\alpha)$=height/radius. The angle of reposes of crystal forms A and B were measured and compared for their difference, respectively. The results are listed in Table 7 below.

TABLE 7

Angle of Repose Data of Crystal Forms A and B of Dexrabeprazole Sodium

| Determination of angle of repose (crystal form A) | Determination of angle of repose (crystal form B) |
|---|---|
| $1^{st}$58.93° | $1^{st}$36.35° |
| $2^{nd}$58.86° | $2^{nd}$36.35° |
| $3^{rd}$58.88° | $3^{rd}$36.34° |
| Average: 58.89° | Average: 36.35° |

Testing results show that the angle of repose data of crystal form B is obviously lower than that of crystal form A. According to the principle and experiences of preparations, when the angle of repose is not greater than 50°, it tends to exhibit powder flowability suitable for the production of preparations. If the angle of repose is too large, the powder flowability may be poor, and thus is less acceptable for the production of preparations.

The compression coefficient and the Hausner ratio closely related thereto are simple and fast methods for predicting the powder property, and are often used as the index for characterizing the powder flowability.

Crystal forms A and B were sampled for measuring the tap density and bulk density of powder of different crystal forms, and then the compression coefficient and the Hausner ratio were calculated. The results are listed in Table 8 below. Wherein, the compression coefficient (%)=[(the tap density−the bulk density)/the tap density×100%; and the Hausner ratio=the tap density/the bulk density.

TABLE 8

Fluidity Data of Various Crystal Forms of Dexrabeprazole Sodium

|  | Crystal form A | Crystal form B |
|---|---|---|
| Tap density (g · cm$^{-3}$) | 0.450 | 0.515 |
| Bulk density (g · cm$^{-3}$) | 0.267 | 0.398 |
| Compression coefficient | 40.67% | 22.72% |
| Hausner ratio | 1.69 | 1.29 |

Testing results show that the compression coefficient and the Hausner ratio of crystal form B are obviously superior to those of crystal form A. The crystal form A has a compression coefficient of greater than 38% and a Hausner ratio of greater than 1.60, which indicates the relatively poor powder flowability of the solid state thereof.

8.2 Mixing Uniformity
Prescription of Preparations:

| Components | Amount |
|---|---|
| Crystal form A or crystal form B of dexrabeprazole sodium | 100 g |
| Starch | 60 g |
| Pre-gelled starch | 120 g |
| Microcrystalline cellulose | 310 g |
| Hydroxypropyl methyl cellulose | 65 g |
| Magnesium oxide | 120 g |
| PVPK30 | 10 g |
| Magnesium stearate | 15 g |

Process of Preparations:
1) Prescribed amounts of dexrabeprazole sodium, starch, pre-gelled starch, microcrystalline cellulose, hydroxypropyl methyl cellulose, and magnesium oxide were taken, respectively, and thoroughly mixed;
2) A prescribed amount of PVPK30 was added to the above mixture for wet granulation (18-mesh sieve). The resultant particles were dried at 50° C. for about 1-2 h, and passed through a 16-mesh sieve to sieve complete particles. Magnesium stearate was additionally introduced, and then the mixture sample was subjected to uniformity examination with a sampling tool at 10, 15, and 20 min respectively. The results are listed in Tables 9 and 10.

The mixing uniformity is measured by high performance liquid chromatography (General Rule 0512, Part IV, Chinese Pharmacopoeia 2015 edition).

Chromatographic condition and system suitability test features as follows: octadecylsilane bonded silica was taken as a filler; 0.05 mol/L phosphate solution (the pH of 0.05 mol/L disodium phosphate solution was adjusted to 7.0 with 0.05 mol/L dipotassium phosphate solution)-methanol (45:55) was taken as a mobile phase; and the detection wavelength was 290 nm. The number of theoretical plates should not be less than 2000 as calculated in accordance with dexrabeprazole sodium peak.

Measurement method: The product (about 80.5 mg) was precisely weighed, and placed in a 100 ml volumetric flask. The mixture was dissolved in an appropriate amount of diluent, subject to ultrasonic treatment, and diluted to the scale. The dilution was shaken to uniform, and filtered. 20 μl of the filtrate was precisely sampled, and injected to the HPLC. The chromatogram was recorded. Separately, a suitable amount of dexrabeprazole sodium control was precisely sampled, and measured in accordance with the same procedure as set forth above. The mixing uniform was calculated based on the peak areas according to the external standard method.

Diluent: 0.05 mol/L sodium hydroxide solution-methanol (40:60)
Instrument: LC-20 HPLC, Shimadu, Japan
XS205 electronic analytical balance, Mettler
SevenMulti S40 pH meter, Mettler

TABLE 9

Uniformity of Mixture Containing Crystal Form A (w/w, %)

|  | 10 min | 15 min | 20 min |
|---|---|---|---|
| A | 13.1 | 12.6 | 12.3 |
| B | 11.7 | 12.9 | 12.7 |
| C | 12.7 | 12.3 | 12.8 |
| D | 12.9 | 12.4 | 12.4 |
| E | 13.0 | 12.8 | 12.7 |
| Average | 12.7 | 12.6 | 12.6 |
| RSD % | 8.9 | 4.0 | 3.2 |

TABLE 10

Uniformity of Mixture Containing Crystal Form B (w/w, %)

|  | 10 min | 15 min | 20 min |
|---|---|---|---|
| A | 12.5 | 12.6 | 12.6 |
| B | 12.1 | 12.5 | 12.6 |
| C | 12.6 | 12.5 | 12.5 |
| D | 12.9 | 12.7 | 12.4 |
| E | 12.0 | 12.6 | 12.5 |
| Average | 12.4 | 12.6 | 12.5 |
| RSD % | 3.0 | 1.9 | 1.4 |

Results and analysis: The mixing uniformity of active pharmaceutical ingredients (APIs) and adjuvants in the preparation containing crystal form B of dexrabeprazole sodium is remarkably superior to that of the preparation containing crystal form A. In the field of preparation, the mixing of APIs with adjuvants is the key step for production of tablets. The mixing uniformity of APIs and adjuvants is an important parameter which directly affects stability and uniformity of content and weight variations of tablets. Due to good powder flowability of crystal form B, RSD is below 2% after the APIs and the adjuvants are mixed for 15 min, which meets the index requirement. Crystal form B of dexrabeprazole sodium is more suitable for preparing solid preparations of dexrabeprazole sodium.

The invention claimed is:
1. A dexrabeprazole sodium compound of Formula (I), wherein the dexrabeprazole sodium compound is crystal form C, which has an XRPD pattern represented by angle 2θ with characteristic peaks at 6.22±0.2°, 12.14±0.2°, 12.46±0.2°, 15.82±0.2°, 18.90±0.2°, 22.38±0.2°, 26.56±0.2°, and 28.06±0.2° when measured by Cu target radiation having a DSC pattern with an exothermic peak at about 234° C.±5° C.

2. A method for preparing the dexrabeprazole sodium compound according to claim 1, comprising the following steps:
 1) dissolving dexrabeprazole sodium in methanol or ethanol, concentrating the mixture to dryness under reduced pressure, and repeating the step at least once;
 2) adding acetonitrile to the residue obtained in step 1), stirring and concentrating the mixture to dryness under reduced pressure; and
 3) adding a solvent toluene or xylene to the residue obtained in step 2), and stirring the mixture for crystallization to obtain the desired compound.

3. The method according to claim 2, comprising one or more of the following features a) to c):
 a) wherein in step 1), the dexrabeprazole sodium is dissolved in methanol;
 b) wherein in step 1), the step is repeated for one to six times; and
 c) wherein in step 3), the stirring the mixture for crystallization is performed under inert gas protection.

4. A pharmaceutical composition, comprising the dexrabeprazole sodium compound according to claim 1 and a pharmaceutically acceptable carrier.

* * * * *